United States Patent [19]
Lui et al.

[11] Patent Number: 6,162,943
[45] Date of Patent: Dec. 19, 2000

[54] METHOD FOR PRODUCING α-ALKOXY-α-TRIFLUOROMETHYL-ARYL ACETIC ESTERS AND -ARYL ACETIC ACIDS

[75] Inventors: Norbert Lui, Köln; Albrecht Marhold, Leverkusen, both of Germany

[73] Assignee: Bayer Aktiengesellschaft, Leverkusen, Germany

[21] Appl. No.: 09/284,689

[22] PCT Filed: Oct. 9, 1997

[86] PCT No.: PCT/EP97/05565

§ 371 Date: Apr. 16, 1999

§ 102(e) Date: Apr. 16, 1999

[87] PCT Pub. No.: WO98/17622

PCT Pub. Date: Apr. 30, 1998

[30] Foreign Application Priority Data

Oct. 22, 1996 [DE] Germany .............. 196 43 592

[51] Int. Cl.[7] .................. C07C 205/06; C07C 69/76; C07C 65/21
[52] U.S. Cl. .................. 560/20; 560/64; 560/100; 560/103; 560/104; 562/434; 562/473; 562/490; 562/493; 562/495
[58] Field of Search ................ 560/20, 64, 100, 560/103, 104; 562/434, 473, 490, 493, 495

[56] References Cited

PUBLICATIONS

J. Org. Chem. 34, No. 9 Sep. 1969, p. 2543., Dale et al., 2–Methoxy . . . Amines.
Tetrahedron, vol. 42, No. 2, (month unavailable) 1986, p. 547, A modified . . . Amino Acid Derivatives.
J. Org. Chem., vol. 57, No. 13, Jun. 1992, p. 3731, Goldberg et al., A new . . . Mosher's Acid.
Synlett, Sep. 1991, pp. 643–644, Ramaiah et al., Direct Trifluoromethylation of α–Keto Esters to B, B–Trifluoroacetic Acid Derivatives using Trifluoronethylsilane.

*Primary Examiner*—Johann Richter
*Assistant Examiner*—Rosalynd Keys
*Attorney, Agent, or Firm*—Joseph C. Gil; Diderico van Eyl

[57] ABSTRACT

Process for the preparation of α-alkoxy-α-trifluoromethylarylacetic esters of the formula (I)

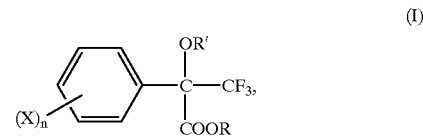

wherein R is a component selected from the group consisting of $C_1$–$C_6$-alkyl, $C_2$–$C_6$-alkenyl, $C_3$–$C_7$-cycloalkyl, $C_6$–$C_{10}$-aryl and $C_1$–$C_6$-halogenoalkyl, R' is selected from the group consisting of $C_1$–$C_4$-alkyl, X is selected from the group consisting of halogen, $C_1$–$C_4$-alkyl, $C_2$–$C_4$-alkenyl, $C_6$–$C_{10}$-aryl or $C_1$–$C_4$-alkoxy and nitro, and n is zero or an integer from 1 to 3.

8 Claims, No Drawings

METHOD FOR PRODUCING α-ALKOXY-α-TRIFLUOROMETHYL-ARYL ACETIC ESTERS AND -ARYL ACETIC ACIDS

BACKGROUND OF THE INVENTION

The present invention relates to an advantageous process for the preparation of α-alkoxy-α-trifluoromethyl-arylacetic esters and -arylacetic acids from arylketo esters. α-Alkoxy-α-trifluoromethyl-arylacetic acids, e.g. α-methoxy-α-trifluoromethyl-phenylacetic acid, also called Mosher's acid, are important reagents for determining the optical purity of chiral amines (see Synlett 1991, 643).

Process for the preparation of α-methoxy-α-trifluoromethyl-phenylacetic acid are known, but all of the known processes are unsatisfactory.

For example, according to J. Org. Chem. 34, 2543 (1969), sodium cyanide is reacted with α,α,α-trifluoroacetophenone in 1,2-dimethoxyethane, then alkylated with dimethyl sulphate, then the nitrile is hydrolysed to give the amide and, finally, the amide is hydrolysed to give the acid. In a variation of this process, instead of the methoxyethane, t-butanol is used and the hydrolyses are carried out using alkaline hydrogen peroxide solution (Tetrahedron 42, 547 (1986)). In both cases, disadvantages are the poor availability of the trifluoroacetophenone, the preparation 20 of which involves the handling of gaseous trifluoroacetyl chloride (boiling point: +2° C.), and the fact that trifluoroacetophenone is only obtainable in moderate yields. In addition, toxic sodium cyanide has to be handled, which signifies extra expenditure, including for disposal. Finally, the hydrolyses produce benzoic acid as secondary component, which because of its ability to sublime, can only be removed with difficulty, as a result of which this method generally only gives products containing benzoic acid.

Another process for the preparation of α-methoxy-α-trifluoromethyl-phenylacetic acid (J. Org. Chem. 57, 3731 (1992)) starts from trimethylsilyl trifluoroacetates and α,α,α-trifluoroacetophenone, which are reacted in the presence of the crown ether 18-crown-6. The trichloromethyl group is then hydrolysed using potassium hydroxide/methanol, again producing benzoic acid as secondary component. As well as the disadvantages described above, which are caused by the use of α,α,α-trifluoroacetophenone and the benzoic acid which forms as secondary component, this process also uses an expensive crown ether, which also causes disposal problems.

Finally, Synlett (loc. cit.) describes the reaction of a-keto esters with trifluoromethyl-trimethylsilane and the hydrolysis of the formed trifluoromethyl trimethylsilyl ether with aqueous hydrochloric acid to give the corresponding trifluoromethylhydroxy compound. If benzyl esters are used, then a reaction time of 69 hours is required for formation of the hydroxyl compound (loc. cit., Table 1, line 4), which is almost 3 whole days. In the case of benzoyl formates (=benzoylalkoxy compounds), it is stated that the hydrolysis of the silyl ester presents problems. A useful synthesis of α-alkoxy-α-trifluoromethyl-arylacetic acids is thus not practicable in this way.

SUMMARY OF THE INVENTION

A process for the preparation of α-alkoxy-α-trifluoromethyl-arylacetic esters of the formula (I)

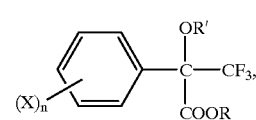

in which
R is $C_1$–$C_6$-alkyl, $C_2$–$C_6$-alkenyl, $C_3$–$C_7$-cycloalkyl, $C_6$–$C_{10}$-aryl or $C_1$–$C_6$-halogenoalkyl,
R' is $C_1$–$C_4$-alkyl,
X is identical or different substituents from the group consisting of halogen, $C_1$–$C_4$-alkyl, $C_2$–$C_4$-alkenyl, $C_6C_{10}$-aryl or $C_1$–$C_4$-alkoxy and nitro and
n is zero or an integer from 1 to 3,
has now been found, which is characterized in that a keto ester of the formula

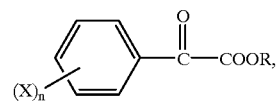

n which
R, X and n are as defined in formula (1),
is reacted with trifluoromethyl-trimethylsilane in the presence of a solvent and of a fluoride at least slightly soluble in the reaction mixture, as catalyst to give a trimethyl silyl ether of the formula (III)

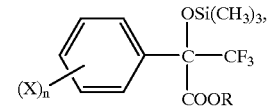

in which
R, X and n are as defined in formula (I),
which is reacted with an alkoxide, or an alcohol which has been rendered alkaline to give the salt of a hydroxyl compound of the formula (IV),

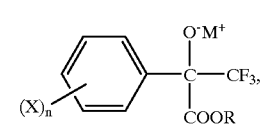

in which
R, X and n are as defined in formula (I), and $M^+$ is the ion of an alkali metal,
which is reacted with an alkylating agent, which converts the $O^-M^+$ group into an OR' group.

Where R is $C_1$–$C_6$-halogenoalkyl, it can, for example, be alkyl groups which are straight-chain or branched and which contain from 1 to 5 identical or different substituents from the group consisting of fluorine, chlorine and bromine.

Preferably, R is straight-chain or branched $C_1$–$C_4$-alkyl, $C_2$–$C_4$-alkenyl, cyclopentyl, cyclohexyl, phenyl or $C_1$–$C_4$-halogenoalkyl which contains from 1 to 5 fluorine and/or chlorine atoms. R is particularly preferably methyl or ethyl.

R' can be straight-chain or branched, and is, for example, methyl, ethyl or isopropyl. It is preferably methyl.

X is preferably identical or different substituents from the group consisting of methyl, chlorine, bromine, ethenyl, phenyl and nitro.

n is preferably 0, 1 or 2, in particular zero.

DETAILED DESCRIPTION OF THE INVENTION

Keto esters of the formula (II) which can be used in the process according to the invention are, for example, available commercially or can be prepared in a known manner or by analogy therewith.

Trifluoromethyl-trimethylsilane is available commercially.

The molar ratio of the keto ester of the formula (II) to trifluoromethyl-trimethylsilane can be, for example, from 1:1 to 1:2. It is preferably from 1:1 to 1:1.5.

Examples of suitable solvents for this reaction are aprotic solvents, such as ethers, alkyl chlorides, amides (including cyclic amides), nitriles and aromatic hydrocarbons. Preference is given to tetrahydrofuran, polyethers of the formula $CH_3O$—$(CH_2$—$CH_2$—$O)_m$—$CH_3$ where m=from 1 to 4, methylene chloride, chloroform, dimethylformamide, N-methylpyrrolidone, acetonitrile and toluene.

The reaction is preferably carried out using largely anhydrous solvents and reactants.

Examples of fluorides which are at least slightly soluble in the reaction mixture and are suitable as catalyst are alkali metal fluorides, alkali metal bifluorides, quaternary onium fluorides, chiral fluorides and tris-(dimethylamino)-sulphonium difluorotrimethylsilicate. Other individual compounds which may be mentioned are: potassium fluoride, caesium fluoride, potassium hydrogenbifluoride, tetrabutylammonium fluoride, tetrabutylammonium hydrogenbifluoride, tetrabutylammonium dihydrogentrifluoride, tetramethylammonium fluoride and tetraethylammonium fluoride, tetraalkylphosphonium fluoride and tetraphenylphosphonium fluoride and N-benzylcinchonium fluoride. Provided it is an organic fluoride, the fluoride catalyst can optionally comprise water of hydration.

Where appropriate, it is additionally possible to use crown ethers, e.g. 18-crown-6 or its adduct with potassium fluoride. The amount of crown ethers can be, for example, from 1 to 20 mol %, based on the fluoride catalyst. When fluorides containing organic groups are used, the use of crown ethers does not generally afford any advantage.

Preferably, use is made of potassium fluoride, caesium fluoride or tetrabutylammonium fluoride, tetrabutylammonium hydrogenfluoride or tetrabutylammonium dihydrogentrifluoride.

If the fluoride catalyst is soluble in a solvent suitable for the reaction, it is also possible to use it in dissolved form, e.g. a solution of tetrabutylammonium fluoride x $3H_2O$ in tetrahydrofuran.

The amount of fluoride catalyst can be, for example, from 0.05 to 30 mol %, preferably from 0.1 to 20 mol %, based on the keto ester of the formula (II).

The reaction of the keto ester of the formula (II) with trifluoromethyl-trimethylsilane can be carried out, for example, at from −40 to 120° C., preferably at 0 to 80° C. The pressure is unimportant. The process can be carried out at atmospheric pressure, increased pressure or reduced pressure. The process is preferably carried out at atmospheric pressure or in a closed vessel at the pressure which establishes by itself at the reaction temperature.

The reaction of the keto ester of the formula (II) with trifluoromethl-trimethylsilane can be carried out, for example, by metering in the silane to an initial charge of the solvent, the keto ester and the catalyst, or by metering the catalyst into an initial charge of the solvent, the keto ester and the silane. Other possible ways of carrying out this reaction are also possible.

When the reaction is complete, if desired, the solvent can be removed, for example by distillation. It is, however, preferable to react the resulting trimethyl silyl ether of the formula (III) in the form of the fully reacted reaction mixture with an alkoxide or an alcohol which has been rendered alkaline.

Examples of suitable alkoxides are aliphatic $C_1$–$C_4$-alkoxides of alkali metals, such as sodium methoxide, sodium ethoxide and potassium t-butoxide. The alkoxides are preferably used in dissolved form in the corresponding alcohol, i.e. for example sodium methoxide dissolved in methanol.

Examples of suitable alcohols which have been rendered alkaline are aliphatic $C_1$–$C_4$-alcohols which have been rendered alkaline using alkali metal hydroxides and/or alkali metal carbonates. Examples which may be mentioned are: mixtures of sodium hydroxide and methanol and also mixtures of potassium carbonate and ethanol.

The alkoxides and the alcohols which have been rendered alkaline are preferably used in as anhydrous a form as possible. Preference is given to using an alkali metal alkoxide in which the alkoxide radical is identical to the OR' group in the keto ester of the formula (II) used.

The amounts of alkoxides or alcohols which have been rendered alkaline can be chosen, for example, such that, based on on the trimethyl silyl ether of the formula (III), from 1 to 5 equivalent % of alkoxide or % of alkaline equivalents in the alcohol which has been rendered alkaline are used. This amount is preferably from 1 to 1.5 equivalent % or % of alkaline equivalents.

If, together with the alkoxide or in the form of the alcohol which has been rendered alkaline, insufficient alcohol has been introduced into the reaction mixture or insufficient solvent is present from the preceding reaction stage, it is advantageous to add further alcohol as solvent in order to obtain a reaction mixture which can be handled easily. Preference is given to using an alcohol whose OR' group corresponds to that of the keto ester of the formula (II) used.

The reaction with the alkoxide or the alcohol which has been rendered alkaline can be carried out, for example, at temperatures in the range from −20 to +120° C., preferably in the range from 0 to 80° C. Here too, the pressure is unimportant. The process can be carried out at atmospheric pressure, increased pressure or reduced pressure. The process is preferably carried out at atmospheric pressure or in a closed vessel at the pressure which establishes by itself at the reaction temperature.

The reaction with the alkoxide or the alcohol which has been rendered alkaline can be carried out advantageously by metering the alkoxide as solution in an alcohol or the alcohol which has been rendered alkaline into the fully reacted reaction mixture of the preceding reaction stage. Other ways of carrying out this reaction are also possible.

When the reaction is complete, it is preferable to remove solvent which is present, for example by stripping off under reduced pressure. It is, however, also possible to use the entire reaction mixture for further conversion.

For the reaction of the obtained salt of a hydroxyl compound of the formula (IV) with an alkylating agent, it is possible to use, for example, alkylating agents known per se, for example methylating agents such as dimethyl sulphate, methyl iodide, methyl bromide, methyl chloride or methyl toluenesulphonate, or ethylating agents such as ethyl iodide or ethyl toluenesulphonate. Based on the hydroxyl compound of the formula (IV) used, it is possible to use, for example, from 1 to 5 equivalents of an alkylating agent. This amount is preferably from 1 to 2 equivalents.

During the reaction, the temperature can be, for example, between 0 and 100° C., preferably it is from 5 to 80° C. If alkylating agents are used which are gaseous at the reaction temperature, it is necessary to work under pressure, for example at up to 10 bar. Otherwise, the pressure is unimportant. The process can, then, be carried out at atmospheric pressure, reduced pressure or increased pressure. Particularly preferably, the alkylating agent used is dimethyl sulphate and the process is carried out at atmospheric pressure.

During the alkylation, the addition of a solvent is not absolutely necessary, particularly if one has already been entrained from the preceding reaction stage. If desired, it is possible to add an inert solvent, for example an ether such as methyl tert-butyl ether or a hydrocarbon such as toluene or hexane.

The reaction can be carried out, for example, by metering the alkylating agent into an initial charge of the salt of the hydroxyl compound of the formula (IV), optionally in the form of the fully reacted reaction mixture obtained in its preparation and optionally solvents. Other ways of carrying out this reaction are also possible. Reaction of the salt of the hydroxyl compound of the formula (IV) can be completed, if necessary, by subsequently adding base. Suitable examples thereof are the abovedescribed alkoxides and aqueous solutions of alkali metal hydroxides.

The reaction mixture can be worked up and the prepared α-alkoxy-α-trifluoromethyl-arylacetic ester of the formula (I) can be isolated by distillation. It is also possible to discharge the reaction mixture into water, if necessary neutralize using an acid (e.g. to a pH in the range from 6 to 8), extract the compound of the formula (I) with a suitable extractant, e.g. methyl tert-methyl ether, and isolate it by stripping off the extractant. The isolated product of the formula (I) can be further purified in a simple manner, for example by distillation. In this connection, in contrast to the prior art, there can be no problems with benzoic acid forming as secondary component. In the case of the process according to the invention, however, benzoic esters may form as secondary component and these, in contrast to benzoic acid, can be removed easily by distillation since they do not have a tendency towards sublimation.

According to the invention, it is also possible to prepare α-alkoxy-α-trifluoromethyl-arylacetic acids of the formula (V)

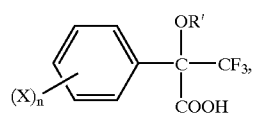

(V)

in which

R', X and n are as defined in formula (I). For this purpose, α-alkoxy-α-trifluoromethyl-arylacetic esters of the formula (I) are firstly prepared as described above, and these are converted into an acid of the formula (V) by hydrolysis or cleavage with an acid.

For the hydrolysis, it is possible to use alkaline or acidic aqueous solutions, e.g. aqueous solutions of alkali metal hydroxides or mineral acids. The customary methods of ester hydrolysis can be used here.

Where appropriate, it is possible to carry out the process in the presence of a diluent, e.g. an alcohol such as methanol.

The cleavage using an acid can be carried out, for example, using formic acid according to the method described in Org. Synth. Coll. Vol. III, 33 (1955).

Preference is given to using the method according to the invention to prepare Mosher's acid (formula (V); R'=CH$_3$, n=zero).

The process according to the invention permits the preparation of α-alkoxy-α-trifluoromethyl-arylacetic esters and -arylacetic acids in a very favourable manner. For example, the reaction times are short, the required reagents are readily available, the handling of toxic sodium cyanide is unnecessary, the secondary component benzoic acid, which can only be removed with difficulty, is unable to form, and the yields and purities of the products are much improved. The esters of the formula (I) are obtainable from keto esters of the formula (II), for example in yields of well above 85% of theory, and the acids of the formula (V) are obtainable from the esters of the formula (I), for example in yields of well over 90% of theory. Added to this is the fact that the esters of the formula (I) can be prepared without isolation of the compounds of the formulae (III) and (IV) in a one-pot process, which signifies only low expenditure on apparatus.

In view of the prior art described at the outset, the positive effects which can be achieved using the process according to the invention are extraordinarily surprising.

The invention is further described in the following illustrative examples. All reference to parts and percentages are by weight unless otherwise indicated.

EXAMPLES

Example 1

A solution of 1 g of tetrabutylammonium fluoride×3H$_2$O in 50 ml of tetrahydrofuran were added dropwise to an initial charge of 164 g of methyl phenylglycoxylate (formula II); R=CH$_3$, n=zero) and 156 g of trifluoromethyl-trimethylsilane dissolved in 400ml of tetrahydrofuran at room temperature under nitrogen. After 3 hours, 216 g of 30% strength by weight sodium methoxide solution in methanol were added dropwise to the resulting reaction mixture, which was then stirred for 1 hour at room temperature. A colourless solid precipitated out. The solvents present were removed under reduced pressure, and then 500 ml of methyl tert-butyl ether were added to the solid which remained, and then 170 g of dimethyl sulphate were added dropwise at 25° C. 25 ml of 20% strength by weight aqueous sodium hydroxide solution were finally added. After 3 hours, 500 ml of water were added, the organic phase was separated off, and the aqueous phase was extracted using methyl tert-butyl ether, dried over sodium sulphate and distilled. 211 g of methyl α-methoxy-α-trifluoromethylphenylacetate were isolated (90% of theory) (b.p.: 62° C/0.03 mm).

Example 2

210 g of methyl α-methoxy-α-trifluoromethylphenylacetate (obtained according to Example 1) were mixed with 600 ml of methanol at 25° C., and 860 ml of 1N aqueous sodium hydroxide solution were slowly added dropwise. The mixture was stirred at room temperature for 5 hours. Dilute aqueous hydrochloric acid was then used to adjust the pH to 1, and extraction was carried out using 2×200 ml of methylene chloride, the organic phase was dried over sodium sulphate and, finally, the solvent was removed. This gave 96% yield of α-methoxy-α-trifluoromethylphenylacetic acid (=190 g).

Although the invention has been described in detail in the foregoing for the purpose of illustration, it is to be understood that such detail is solely for that purpose and that variations can be made therein by those skilled in the art without departing from the spirit and scope of the invention.

What is claimed is:

1. Process for the preparation of α-alkoxy-α-trifluoromethyl-arylacetic esters of the formula (I)

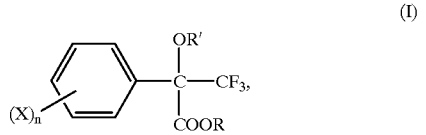
(I)

wherein
R is selected from the group consisting of $C_1$–$C_6$-alkyl, $C_2$–$C_6$-alkenyl, $C_3$–$C_7$-cycloalkyl, $C_6$–$C_{10}$-aryl and $C_1$–$C_6$-halogenoalkyl,
R' is selected from the group consisting of $C_1$–$C_4$-alkyl,
X is selected from the group consisting of halogen, $C_1$–$C_4$-alkyl, $C_2$–$C_4$-alkenyl, $C_6$–$C_{10}$-aryl or $C_1$–$C_4$-alkoxy and nitro, and
n is zero or an integer from 1 to 3;
the process comprising the steps of
A) reacting (a) a keto ester of the formula (II)

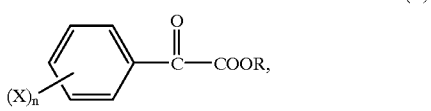
(II)

wherein R, X and n are as defined in formula (I),
with (b) trifluoromethyl-trimethylsilane in the presence of (c) a solvent and (d) a fluoride that is at least slightly soluble in the reaction mixture as a catalyst to form a trimethyl silyl ether of the formula (III)

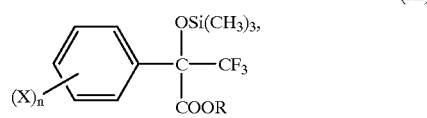
(III)

wherein R, X and n are defined as in formula (I),
B) reacting the trimethyl ether having formula (III) with an alkoxide, or an alcohol which has been rendered alkaline to give a salt of the compound of the formula (IV),

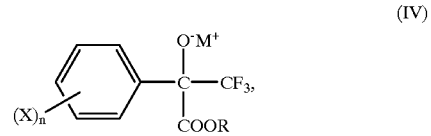
(IV)

wherein R, X and n are as defined in formula (I), and $M^+$ is the ion of an alkali metal, and C) reacting the compound having the formula (IV) with an alkylating agent, to convert the $O^-M^+$ group into an OR' group.

2. Process according to claim 1, wherein R is selected from the group consisting of straight-chain or branched $C_1$–$C_4$-alkyl, $C_2$–$C_4$-alkylene, cyclopentyl, cyclohexyl, phenyl and $C_1$–$C_4$-halogenoalkyl having from 1 to 5 fluorine or chlorine atoms,
R' is methyl, ethyl or isopropyl,
X is selected from the group consisting of methyl, chlorine, bromine, ethenyl, phenyl and nitro,
n is zero, 1 or 2.

3. Process according to claim 1, wherein the molar ratio of the keto compound of the formula (II) to trifluoromethyl-trimethylsilane is from 1:1 to 1:2, the solvent used for the reaction of the keto compound of the formula (II) with trifluoromethyl-trimethylsilane is an aprotic solvent, the fluoride catalyst used is from 0.05 to 30 mol %, based on the keto ester of the formula (II), of alkali fluorides, alkali metal bifluorides, quaternary onium fluorides, chiral fluorides or tris(dimethylamino)-sulphonium difluorotrimethylsilicate, and the reaction of the keto ester of the formula (II) with trifluoromethyl-trimethylsilane is carried out at from −40 to +1 20° C.

4. Process according to claim 1, wherein the alkoxides used are aliphatic $C_1$–$C_4$-alkoxides of alkali metals, or the alcohols rendered alkaline used are aliphatic $C_1$–$C_4$-alcohols which have been rendered alkaline using alkali metal hydroxides and/or alkali metal carbonates, the alkoxides or the alcohols which have been rendered alkaline are used in an amount of from 1 to 5 equivalent %, based on the trimethyl silyl ether of the formula (III), and the reaction with the alkoxide or the alcohol which has been rendered alkaline is carried out at from 0 to 80° C.

5. Process according to claim 1, wherein the alkylating agents used are methylating agents or ethylating agents in an amount of from 1 to 5 equivalents, based on the salt of a hydroxyl compound of the formula (IV), and the alkylation is carried out at a temperature ranging from 0 to 100° C.

6. Process according to claim 1, wherein in order to obtain the prepared α-alkoxy-α-trifluoromethyl-arylacetic ester of the formula (I), the reaction mixture produced after alkylation is isolated by distillation or by discharge into water, neutralization with an acid, extraction with a suitable solvent and removal of the extractant.

7. Process according to claim 1, wherein the α-alkoxy-α-trifluoro methyl-arylacetic ester of the formula (I) isolated from the alkylation reaction mixture is further purified by distillation.

8. The process of claim 1 further comprising the step of converting α-alkoxy-α-trifluoromethyl-arylacetic esters of the formula (I) into an α-alkoxy-α-trifluoromethyl-arylacetic acid of the formula (V)

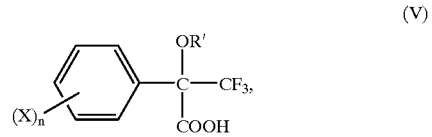
(V)

by hydrolysis or cleavage with an acid, wherein R', X and n are as defined in formula (I) in claim 1.

* * * * *